US008586314B2

(12) United States Patent
Stender

(10) Patent No.: US 8,586,314 B2
(45) Date of Patent: Nov. 19, 2013

(54) **PEPTIDE NUCLEIC ACID PROBES FOR DETECTION, IDENTIFICATION AND/OR QUANTITATION OF *PSEUDOMONAS* (SENSU STRICTO)**

(75) Inventor: Henrik Stender, Gentofte (DK)

(73) Assignee: AdvanDx, Inc., Woburn, MA (US)

( * ) Notice: Subject to any disclaimer, the term of this patent is extended or adjusted under 35 U.S.C. 154(b) by 498 days.

(21) Appl. No.: 12/752,480

(22) Filed: Apr. 1, 2010

(65) Prior Publication Data

US 2010/0285987 A1 Nov. 11, 2010

Related U.S. Application Data

(63) Continuation of application No. 10/821,805, filed on Apr. 8, 2004, now abandoned, and a continuation-in-part of application No. 10/719,979, filed on Nov. 21, 2003, now abandoned.

(60) Provisional application No. 60/428,554, filed on Nov. 22, 2002.

(51) Int. Cl.
*C12Q 1/68* (2006.01)
*C12M 1/34* (2006.01)
*C07H 21/04* (2006.01)

(52) U.S. Cl.
USPC ..... 435/6.15; 435/6.11; 435/6.12; 435/287.2; 536/24.32

(58) Field of Classification Search
None
See application file for complete search history.

(56) References Cited

U.S. PATENT DOCUMENTS

| | | | |
|---|---|---|---|
| 5,527,675 A | 6/1996 | Coull et al. | 435/6 |
| 5,539,082 A | 7/1996 | Nielsen et al. | 530/300 |
| 5,623,049 A | 4/1997 | Lobberding et al. | 530/300 |
| 5,714,331 A | 2/1998 | Buchardt et al. | 435/6 |
| 5,736,336 A | 4/1998 | Buchardt et al. | 435/6 |
| 5,773,571 A | 6/1998 | Nielsen et al. | 530/300 |
| 5,786,461 A | 7/1998 | Buchardt et al. | 536/18.7 |
| 5,837,459 A | 11/1998 | Berg et al. | 435/6 |
| 5,891,625 A | 4/1999 | Buchardt et al. | 435/6 |
| 5,972,610 A | 10/1999 | Buchardt et al. | 435/6 |
| 5,986,053 A | 11/1999 | Ecker et al. | 435/6 |
| 6,107,470 A | 8/2000 | Nielsen et al. | 536/23.1 |
| 6,110,676 A | 8/2000 | Coull et al. | 435/6 |
| 6,169,169 B1 * | 1/2001 | Hyldig-Nielsen et al. | 536/22.1 |
| 6,355,421 B1 | 3/2002 | Coull et al. | 435/6 |
| 6,357,163 B1 | 3/2002 | Buchardt et al. | 43/6 |
| 6,361,942 B1 | 3/2002 | Coull et al. | 435/6 |
| 6,485,901 B1 | 11/2002 | Gildea et al. | 435/5 |
| 6,664,045 B1 | 12/2003 | Hyldig-Nielsen et al. | 435/6 |

FOREIGN PATENT DOCUMENTS

WO WO 9947706 A1 * 9/1999

OTHER PUBLICATIONS

Ludwig, W. et al. Applied and Environmental Microbiology 60(9):3236 (Sep. 1994).*
Locatelli, L. et al. Systemic and Applied Microbiology 25:220-227 (Aug. 2002).*
Altschul et al. Polyamide based nucleic acid analogs- synthesis of d-amino acids with nucleic acid bases bearing side chains. Nucleic Acids Res. 25:3389-3402 (1997).
Anzai Y. et al., Phylogenetic affiliation of the *Pseudomonads* based on 16S rRNA sequence. Int. J. Syst. Bacteriol. 50:1563-1589 (2000).
Egholm et al. PNA hybridizes to complementary oligonucleotides obeying the Watson-Crick hydrogen-bonding rules. *Nature* 365:566-568 (1993).
Guo et al., Enhanced discrimination of single nucleotide polymorphisms by artificial mismatch hybridization. Nature Biotechnology 15: 331-335 (1997).
Kempf et al. Fluorescent in situ hybridization allows rapid identification of microorganisms in blood cultures. *J. Clin. Microbial* 38:830-838 (2000).
Kersters K. et al. Recent changes in the classification of the *Pseudomonads*: an overview. System. Appl. Microbiol. 19:465-477 (1996).
O'Keefe et al. Filter-based PNA in situ hybridization for rapid detection, identification and enumeration of specific micro-organisms. *J. Appl. Microbiol.* 90:180-189) (2001).
Rigby et al. Fluorescence in situ hybridization with peptide nucleic acid probes for rapid identification of *Candida albicans* directly from blood culture bottles. *J. Clin. Microbiol.* 40:2182-2186 (2002).
Stender, H. et al. Direct detection and identification of *Mycobacterium tuberculosis* in smear-positive sputum samples by fluorescence in situ hybridization (FISH) using peptide nucleic acid (PNA) probes. *Int. J. Tuberc. Lung Dis.* 3:830-837 (1999).
Stender et al. Fluorescence in situ hybridization assay using peptide nucleic acid probes for differentiation between tuberculous and nontuberculous *Mycobacterium* species in smears of *Mycobacterium* cultures. *J. Clin. Microbiol.* 37:2760-2765 (1999).
Stender et al. Rapid detection, identification, and enumeration of *Pseudomonas aeruginosa* in bottled water using peptide nucleic acid probes. *J. Microbiol. Methods* 42:245-253 (2000).
Stender et al. Combination of ATP-bioluminescence and PNA probes allows rapid total counts and identification of specific microorganisms in mixed populations. *J. Microbiol. Methods* 46:69-75 (2001).
Stender et al. Rapid detection, identification, and enumeration of *Escherichia coli* by fluorescence in situ hybridization using an array scanner. *J. Microbiol. Methods* 45: 31-39 (2001).

(Continued)

*Primary Examiner* — Diana Johannsen
(74) *Attorney, Agent, or Firm* — McCarter & English, LLP; Jonathan M. Sparks

(57) ABSTRACT

Disclosed is a PNA probe that includes a nucleobase sequence suitable for the detection, identification and/or quantitation of *Pseudomonas* (sensu stricto). In one embodiment, the PNA probe is complementary to a target sequence of 23S rRNA or rDNA from all species of the genus *Pseudomonas*. The invention has a wide range of important uses including detecting *Pseudomonas* in a sample of interest.

13 Claims, No Drawings

(56) References Cited

OTHER PUBLICATIONS

Woese, Bacterial evolution. *Microbial. Rev.* 51:221-271 (1987).

Wordon et al. In situ hybridization of *Prochlorococcus* and *Synechococcus* (marine cyanobacteria) spp. with RRNA-targeted peptide nucleic acid probes. *Appl. Environ. Microbiol.* 66:284-289 (2000).

Oliveira, K. et al.: "Rapid Identification of *Staphylococcus aureus* Directly from Blood Cultures by Fluorescence in Situ Hybridization with Peptide Nucleic Acid Probes"; J. Clin. Microbiol. 40:247-251 (2002).

Palleroni, N.J.: "Present situation of the taxonomy of aerobic *Pseudomonads*"; *Pseudomonas* Molecular Biology and Biotechnology, Part 3. Taxonomy and Identification, Chapter 13; American Society for Microbiology (1992); pp. 105-115.

Stender, H. et al.: "PNA for rapid microbiology"; Journal of Microbiological Methods 48 (2002; pp. 1-17.

\* cited by examiner

PEPTIDE NUCLEIC ACID PROBES FOR DETECTION, IDENTIFICATION AND/OR QUANTITATION OF *PSEUDOMONAS* (SENSU STRICTO)

CROSS-REFERENCE TO RELATED APPLICATIONS

The present application is a continuation of U.S. application Ser. No. 10/821,805, filed on Apr. 8, 2004, now abandoned, which application is a continuation-in-part of U.S. application Ser. No. 10/719,979, filed on Nov. 21, 2003, now abandoned, which application claims the benefit of Provisional Application No. 60/428,554, filed on Nov. 22, 2002, the entirety of which are herein incorporated by reference.

The present invention relates to peptide nucleic acid (PNA) probes and methods for the analysis of *Pseudomonas* (sensu stricto) optionally present in a sample. The invention further relates to diagnostic kits comprising such PNA probes.

BACKGROUND OF THE INVENTION

Detection, identification and quantitation of specific microorganisms is fundamental to many areas of microbiology ranging from the detection of pathogens in samples of human origin, to spoilage organisms or pathogens in food and beverages and environmental contaminants in municipal water. There are numerous examples where antibiotic treatment is instituted before the infectious agent has been confirmed, food is released for consumption before the microbiological test results are available, or municipal water is distributed via pipelines to the public while culture-based tests are still incubating. The requirement for rapid and accurate test results is obvious.

Comparative analysis of ribosomal RNA (rRNA) sequences or genomic DNA sequences corresponding to said rRNA (rDNA) has become a widely accepted method for establishing phylogenetic relationships between bacterial species (Woese, *Microbiol. Rev.* 51:221-271 (1987)), and Bergey's Manual of systematic bacteriology has been revised based on rRNA or rDNA sequence comparisons.

Ribosomal RNA or rDNA sequence differences between closely related species enable design of specific probes for microbial identification and thus enable diagnostic microbiology to be based on a single genetic marker rather than a series of phenotypic markers as characterizing traditional microbiology (Delong et al., *Science* 342:1360-1363 (1989)).

The taxonomy of the genus *Pseudomonas* has been changed in recent years, such that many species previously classified as *Pseudomonas* species have been reclassified and now belongs to other genera, such as *Burkholderia, Xanthomonas, Aeromonas, Brevundimonas* etc. However many current methods, such as *Pseudomonas* specific growth media, are still based on the former taxonomy, such the microorganisms identified as *Pseudomonas* (sensu stricto) in fact may be former *Pseudomonas* species not longer belonging to the *Pseudomonas* genus (Pacheco & Sage, Abstract, Annual Meeting of the American Society for Microbiology, Salt Lake City, May 2002). There is therefore a need for novel identification methods reflecting the revised taxonomy of the genus *Pseudomonas*.

Despite its name, Peptide Nucleic Acid (PNA) is neither a peptide nor a nucleic acid, it is not even an acid. PNA is a non-naturally occurring polyamid that can hybridize to nucleic acid (DNA and RNA) with sequence specificity (See: U.S. Pat. No. 5,539,082) and Egholm et al., *Nature* 365:566-568 (1993)) according to Watson-Crick base paring rules. However, whereas nucleic acids are biological materials that play a central role in the life of living species as agents of genetic transmission and expression, PNA is a recently developed totally artificial molecule, conceived in the minds of chemists and made using synthetic organic chemistry. PNA also differs structurally from nucleic acid. Although both can employ common nucleobases (A, C, G, T, and U), the backbones of these molecules are structurally diverse. The backbones of RNA and DNA are composed of repeating phosphodiester ribose and 2-deoxyribose units. In contrast, the backbones of the most common PNAs are composed on (aminoethyl)-glycine subunits. Additionally, in PNA the nucleobases are connected to the backbone by an additional methylene carbonyl moiety. PNA is therefore not an acid and therefore contains no charged acidic groups such as those present in DNA and RNA. The non-charged backbone allows PNA probes to hybridize under conditions that are destabilizing to DNA and RNA. Attributes that enable PNA probes to access targets, such as highly structured rRNA and double stranded DNA, known to be inaccessible to DNA probes (See: Stephano & Hyldig-Nielsen, IBC Library Series Publication #948. International Business Communication, Southborough, Mass., pp. 19-37 (1997)). PNAs are useful candidates for investigation when developing probe-based hybridization assays because they hybridize to nucleic acids with sequence specificity. However, PNA probes are not the equivalent of nucleic acid probes in structure or function.

There is a need in the field for effective PNA probes that can be used to analyze *Pseudomonas* (sensu stricto) in a wide range of samples. PNA probes targeting *Pseudomonas aeruginosa* have previously been described (Stender et al., *J. Microbiol. Methods* 42:245-253 (2000), however the heterogenicity of the species within the genus *Pseudomonas* complicates the design of specific PNA probes targeting all species of the genus *Pseudomonas*.

SUMMARY OF THE INVENTION

This invention is directed to PNA probes and their design as well as methods and kits useful for analysis of *Pseudomonas* (sensu stricto) optionally present in a sample of interest. In accordance with claim 1, for instance, the PNA probes are directed to 23S rRNA or the genomic sequences corresponding to said rRNA (rDNA) or its complement.

These PNA probes have the inherent physico/chemical characteristics of PNA probes as compared to nucleic acid probes, such that rapid and accurate analysis can be performed using just a single PNA probe. Furthermore, PNA probes also offers an advantage as compared to nucleic acid probes when applied in fluorescence in situ hybridization assays. Where nucleic acid probes require fixation and permeabilization with cross-linking agents and/or enzymes (for example see Kempf et al., *J. Clin. Microbiol* 38:830-838 (2000)), these PNA probes can be applied directly following smear preparation.

Accordingly, and in one aspect, the invention features a PNA probe that includes a nucleobase sequence suitable for the detection, identification and/or quantitation of *Pseudomonas* (sensu stricto). In one embodiment, the PNA probe is complementary to a target sequence of 23S rRNA or rDNA (or its complement) obtained from essentially any species of the genus *Pseudomonas*. An important feature of the invention is that such probes can be used to detect, identify and/or quantitate nearly any species of *Pseudomonas* as outlined below.

Such selectivity for *Pseudomonas* is accomplished through use of a single probe sequence rather than use of a less specific prior probes and probe sets.

In a preferred embodiment, these PNA probes have a relative short nucleobase sequence, such as 15 nucelobases as illustrated in example 1, whereas nucleic acid probes due to their lower Tm values typically have at least 18 nucleobases (For example see Kempf et al., *J. Clin. Microbiol* 38:830-838 (2000)). A difference that provides these PNA probes with better discrimination to closely related non-target sequences with a single or just a few nucleobase difference(s).

In another aspect, the invention features a method for the detection, identification and/or quantitation of *Pseudomonas* (sensu stricto) in a sample. In one embodiment, the method includes: a) contacting at least one of the PNA probes of claims 1-12 to the sample, b) hybridizing the PNA probe to a target sequence of species of the genus *Pseudomonas* in the sample; and c) detecting the hybridization as being indicative of presence, identity and/or amount of *Pseudomonas* (sensu stricto) in the sample.

In one example, the method comprises contacting a sample with a PNA probe having a probing nucleobase sequence of CCT ACC ACC TTA AAC (Seq. Id. No. 1) and the complements thereof. According to this invention embodiment, the presence, absence and/or number of *Pseudomonas* (sensu stricto) organisms in the sample are then detected, identified and/or quantitated by correlating the hybridization, under suitable hybridization conditions, of the probing nucleobase sequence of the probe to the target sequence. Consequently, the presence, absence and/or number of *Pseudomonas* (sensu stricto) organisms in the sample are determined by direct or indirect detection of the probe/target sequence hybrid.

In still another embodiment, this invention is directed to kits suitable for performing an assay that detect, identify and/or quantitate *Pseudomonas* (sensu stricto) optionally present in a sample. The kits of this invention comprise one or more PNA probes and other reagents or compositions that are selected to perform an assay or otherwise simplify the performance of an assay.

Thus in one invention embodiment, the kit is suitable to detect, identify and/or quantitate *Pseudomonas* (sensu stricto) in a sample in which the kit includes a) at least one PNA probe as defined herein and b) other reagents or compositions necessary to perform the assay such as, but not limited to, buffers, stabilizers, water and the like as well as directions for using the kit.

Those of ordinary skill in the art will appreciate that a suitable PNA probe need not have exactly these probing nucleobase sequences to be operative but often modified according to the particular assay conditions. For example, shorter PNA probes can be prepared by truncation of the nucleobase sequence if the stability of the hybrid needs to be modified to thereby lower the Tm and/or adjust for stringency. Similarly, the nucleobase sequence may be truncated by one end and extended by the other end as long as the discriminating nucleobases remain within the sequence of the PNA probe. Such variations of the probing nucleobase sequences within the parameters described herein are considered to be embodiments of this invention.

The PNA probe, methods and kits of this invention are both sensitive and specific for *Pseudomonas* (sensu stricto). Moreover, the assays described herein are rapid (less than 3 hours) and capable of analysis of *Pseudomonas* (sensu stricto) in a single assay.

Those of ordinary skill in the art will also appreciate that the complement probing sequence is equally suitable for assays, such as but not limited to real-time PCR, that are using rDNA as target.

DETAILED DESCRIPTION OF THE INVENTION

I. Definitions a. As used herein, the term "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids.

b. As used herein, the term "nucleobase sequence" means any segment of a polymer that comprises nucleobase-containing subunits. Non-limiting examples of suitable polymers or polymer segments include oligodeoxynucleotides, oligoribonucleotides, peptide nucleic acids, nucleic acid analogs, nucleic acid mimics, and/or chimeras.

c. As used herein, the term "target sequence" means the nucleobase sequence that is to be detected in an assay.

d. As used herein, the term "probe" means a polymer (e.g. a DNA, RNA, PNA, chimera or linked polymer) having a probing nucleobase sequence that is designed to sequence-specifically hybridize to a target sequence of a target molecule of an organism of interest.

e. As used herein, "analyzed" means that the individual bacteria are marked for detection, identification and/or quantitation and/or for determination of resistance to antibiotics (antimicrobial susceptibility).

f. As used herein, the term "peptide nucleic acid" or "PNA" means any oligomer, linked polymer or chimeric oligomer, comprising two or more PNA subunits (residues), including any of the polymers referred to or claimed as peptide nucleic acids in U.S. Pat. Nos. 5,539,082, 5,527,675, 5,623,049, 5,714,331, 5,736,336, 5,773,571, 5,786,461, 5,837,459, 5,891,625, 5,972,610, 5,986,053, 6,107,470 and 6,357,163. In the most preferred embodiment, a PNA subunit consists of a naturally occurring or non-naturally occurring nucleobase attached to the aza nitrogen of the N-[2-(aminoethyl)]glycine backbone through a methylene carbonyl linkage.

g. As used herein, the terms "label" and "detectable moiety" are interchangeable and shall refer to moieties that can be attached to a probe to thereby render the probe detectable by an instrument or method.

h. As used herein, the term "locked nucleic acid" or "LNA" means any oligomer, linked polymer or chimeric oligomer, comprising one or more LNA subunits (residues), including any of the polymers referred to or claimed as locked nucleic acids, and nucleic acid analogs in U.S. Pat. Nos. 6,639,059, 6,670,461, United States Patent Application numbers US2003077609 A1, US2003224377 A1, US2003082807 A1 and World Patent Office Document number WO03095467. In the most preferred embodiment, a LNA subunit consists of a naturally occurring or non-naturally occurring ribonucleoside in which the 4' oxygen is joined to the 2' carbon through a methylene linkage.

i. Reference herein to "all species of the genus *Pseudomonas*", or a related phrase means essentially all species of that genus described in the "Approved lists of bacterial names." Int. J. Syst. Bacteriol. (1980) 30:225-420 with subsequent revisions published in Int. J. Syst. Bacteriol. with the exception of *Pseudomonas pertucinogena* (see Example 2)

2. Description

I. General:

PNA Synthesis:

Methods for the chemical assembly of PNAs are well known (see: U.S. Pat. Nos. 5,539,082, 5,527,675, 5,623,049, 5,714,331, 5,736,336, 5,773,571, 5,786,461, 5,837,459, 5,891,625, 5,972,610, 5,986,053 and 6,107,470).

PNA Labeling:

Preferred non-limiting methods for labeling PNAs are described in U.S. Pat. Nos. 6,110,676, 6,361,942, 6,355,421, the examples section of this specification or are otherwise well known in the art of PNA synthesis and peptide synthesis.

Labels:

Non-limiting examples of detectable moieties (labels) suitable for labeling PNA probes used in the practice of this invention would include a dextran conjugate, a branched nucleic acid detection system, a chromophore, a fluorophore, a spin label, a radioisotope, an enzyme, a hapten, an acridinium ester and a chemiluminescent compound.

Other suitable labeling reagents and preferred methods of attachment would be recognized by those of ordinary skill in the art of PNA, peptide or nucleic acid synthesis.

Preferred haptens include 5 (6)-carboxyfluorescein, 2,4-dinitrophenyl, digoxigenin, and biotin.

Preferred fluorochromes (fluorophores) include 5 (6)-carboxyfluorescein (Flu), 6-((7-amino-4-methylcoumarin-3-acetyl)amino) hexanoic acid (Cou), 5 (and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.), JOE, Tamara or the Alexa dye series (Molecular Probes, Eugene, Oreg.).

Preferred enzymes include polymerases (e.g. Taq polymerase, Klenow PNA polymerase, T7 DNA polymerase, Sequenase, DNA polymerase 1 and phi29 polymerase), alkaline phosphatase (AP), horseradish peroxidase (HRP) and most preferably, soy bean peroxidase (SBP).

Unlabeled Probes:

The probes that are used for the practice of this invention need not be labeled with a detectable moiety to be operable within the methods of this invention, for example when attached to a solid support

Self-Indicating (or Reporting) Probes:

Beacon probes are examples of self-indicating probes which include a donor moiety and a acceptor moiety. The donor and acceptor moieties operate such that the acceptor moieties accept energy transferred from the donor moieties or otherwise quench signal from the donor moiety. Though the previously listed fluorophores (with suitable spectral properties) might also operate as energy transfer acceptors, preferably, the acceptor moiety is a quencher moiety. Preferably, the quencher moiety is a non-fluorescent aromatic or heteroaromatic moiety. The preferred quencher moiety is 4-((-4-(dimethylamino)phenyl)azo)benzoic acid (dabcyl). In a preferred embodiment, the self-indicating Beacon probe is a PNA Linear Beacon as more fully described in U.S. Pat. No. 6,485,901.

In another embodiment, the self-indicating probes of this invention are of the type described in WIPO patent application WO97/45539. These self-indicating probes differ as compared with Beacon probes primarily in that the reporter must interact with the nucleic acid to produce signal.

Spacer/Linker Moieties:

Generally, spacers are used to minimize the adverse effects that bulky labeling reagents might have on hybridization properties of probes. Preferred spacer/linker moieties for the nucleobase polymers of this invention consist of one or more aminoalkyl carboxylic acids (e.g. aminocaproic acid), the side chain of an amino acid (e.g. the side chain of lysine or ornithine), natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Preferably, such linker moieties will includes less than about 10 subunits, preferably less than about 8 subunits, with about 1 to about 5 subunits being useful for many applications.

Hybridization Conditions/Stringency:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target sequence combination is often found by the well known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions:

Generally, the more closely related the background causing nucleic acid contaminates are to the target sequence, the more carefully stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result.

Aided by no more than routine experimentation and the disclosure provided herein, those of skill in the art will easily be able to determine suitable hybridization conditions for performing assays utilizing the methods and compositions described herein. Suitable in-situ hybridization or PCR conditions comprise conditions suitable for performing an in-situ hybridization or PCR procedure. Thus, suitable in-situ hybridization or PCR conditions will become apparent to those of skill in the art using the disclosure provided herein, with or without additional routine experimentation.

Blocking Probes:

Blocking probes are nucleic acid or non-nucleic acid probes that can be used to suppress the binding of the probing nucleobase sequence of the probing polymer to a non-target sequence. Preferred blocking probes are PNA probes (see: U.S. Pat. No. 6,110,676). It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with the methods, kits and compositions of this invention to suppress the binding of the probes to a non-target sequence that might be present and interfere with the performance of the assay.

Blocking probes are particularly advantageous in single base discrimination.

Probing Nucleobase Sequence:

The probing nucleobase sequence of a probe of this invention is the specific sequence recognition portion of the construct. Therefore, the probing nucleobase sequence is a nucleobase sequence designed to hybridize to a specific target sequence wherein the presence, absence or amount of the target sequence can be used to directly or indirectly detect the presence, absence or number of organisms of interest in a sample. Consequently, with due consideration to the requirements of a probe for the assay format chosen, the length and sequence composition of the probing nucleobase sequence of the probe will generally be chosen such that a stable complex is formed with the target sequence under suitable hybridization conditions.

The preferred probing nucleobase sequence of the probes of this invention that are suitable for the analysis of *Pseudomonas* (sensu stricto) comprise a nucleobase sequence CCT ACC ACC TTA AAC (Seq. Id No. 1) and the complements thereto.

This invention contemplates that variations in these identified probing nucleobase sequences shall also provide probes that are suitable for the detection, identification and/or quantitation of *Pseudomonas* (sensu stricto). Variation of the probing nucleobase sequences within the parameters described herein is considered to be an embodiment of this invention.

Common variations include, deletions, insertions and frame shifts. Additionally, a shorter probing nucleobase sequence can be generated by truncation of the sequence identified above.

A probe of this invention will generally have a probing nucleobase sequence that is exactly complementary to the target sequence. Alternatively, a substantially complementary probing nucleobase sequence might be used since it has been demonstrated that greater sequence discrimination can be obtained when utilizing probes wherein there exists one or more point mutations (base mismatch) between the probe and the target sequence (See: Guo et al., Nature Biotechnology 15: 331-335 (1997)). Consequently, the probing nucleobase sequence may be only 90% homologous to the probing nucleobase sequences identified above. Substantially complementary probing nucleobase sequence within the parameters described above is considered to be an embodiment of this invention.

Complements of the probing nucleobase sequence are considered to be an embodiment of this invention, since it is possible to generate a suitable probe if the target sequence to be detected has been amplified or copied to thereby generate the complement to the identified target sequence.

Detection, Identification and/or Enumeration:

By detection is meant analysis for the presence or absence of the organism optionally present in the sample. By identification is meant establishment of the identity of the organism by genus and species name. By quantitation is meant enumeration of the organisms in a sample. Some assay formats provide simultaneous detection, identification and enumeration (for example see Stender, H. et al., *J. Microbiol. Methods*. 45:31-39 (2001), others provide detection and identification (for example see Stender, H. et al., *Int. J. Tuberc. Lung Dis.* 3:830-837 (1999) and yet other assay formats just provide identification (for example see Oliveira, K et al. *J. Clin. Microbiol.* 40:247-251 (2002)).

Antibiotic Resistance

By determination of resistance to antibiotics is meant analysis of an organism susceptibility to antibiotics based on specific genes or mutations associated with resistance or susceptibility to antimicrobial agents.

As discussed, in one aspect the invention relates to a PNA probe that includes a nucleobase sequence suitable for the detection, identification and/or quantitation of *Pseudomonas* (sensu stricto) in which a preferred embodiment features a PNA probe (or complement thereof) that is complementary to a target sequence of 23S rRNA or rDNA of essentially all species of the genus *Pseudomonas*. Preferred PNA probes will have a length that is generally less than about 30 to about 35 subunits, preferably less than about 20 subunits with between from about 12 to about 18 subunits being preferred for many applications.

By the phrase "complementary" is meant relatively close relationship between the sequence of the PNA probe and its intended nucleic acid template sequence. The percent complementarity between a particular sequence and its template as described in this application can be determined by standard procedures. The degree of complementarity between two sequences can be expressed in a variety of formats including the percentage of homology or identity.

For instance, to determine the percent homology of nucleic acid sequences, the sequences are aligned for optimal comparison purposes (e.g., gaps can be introduced in the sequence of a first nucleic acid sequence for optimal alignment with a second nucleic acid sequence). The nucleotides at corresponding positions are then compared. When a position in the first sequence is occupied by the same nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions). multiplied by.100). In one embodiment the two sequences are the same length.

To determine percent homology between two sequences, the algorithm of Karlin and Altschul (1990) Proc. Natl. Acad Sci. USA 87:2264-2268, modified as in Karlin and Altschul (1993) Proc. Natl. Acad. Sci. USA 90:5873-5877 is used. Such an algorithm is incorporated into the NBLAST and XBLAST programs of Altschul, et al. (1990) J. Mol. Biol. 215:403-410. BLAST nucleotide searches are performed with the NBLAST program, score=100, wordlength=12 to obtain nucleotide sequences homologous to a nucleobase sequence described herein. To obtain gapped alignments for comparison purposes, Gapped BLAST is utilized as described in Altschul et al. (1997) Nucleic Acids Res. 25:3389-3402. When utilizing BLAST and Gapped BLAST programs, the default parameters of the respective programs (e.g., XBLAST and NBLAST) are used.

Such manipulations are readily adapted to determine the percent homology between a PNA probe sequence and its corresponding target nucleic acid template. Sequences that are completely homologous with respect to one another are sometimes referred to herein as being "identical".

Accordingly, and in one embodiment, at least a portion of one or more of the foregoing probes is at least about 90% identical to the *Pseudomonas* target sequence, preferably at least about 95% identical, more preferably at least about 98% to 100% identical to that sequence. By "at least a portion" of the probe is meant generally less than about 14 subunits, preferably between from about 9 to about 14 subunits such as about 10 to about 13 subunits.

A generally preferred PNA probe for many invention applications includes (or in some embodiments essentially consists of) the following sequence: CCT ACC ACC TTA AAC as well as the complement of that sequence. Sometimes the sequence (and its complement) is referred to as a "preferred probing nucleobase" sequence or related phrase.

Although not usually preferred, the preferred probing nucleobase sequence may include additional PNA, DNA or LNA subunits, for instance, added to an end of the sequence, to both ends of the sequence, and/or between the ends (eg., 1, 2, 3, up to about 5, 6, 7 or 8 PNA subunits) in some cases. In such embodiments, the resulting sequence preferably exhibits good hybridization to the intended *Pseudomonas* target sequence. That is, hybridization is not substantially impaired when compared to hybridization under the same conditions with the preferred probing nucleobase sequence. Specific binding between a given PNA probe and the target sequence can be monitored by a variety of suitable techniques such as those described in Stender H et al. PNA for rapid microbiology. J Microbiol Methods. 2002 January; 48(1):1-17. Such methods further include determining the difference in Tm (ΔTm) between the probe and target sequence and the probe and non-target sequence(s).

A variety of hybridization conditions have been described in detail in Williams B et al, PNA fluorescent in situ hybridization for rapid microbiology and cytogenetic analysis.

One or more deletions, substitutions (or both) of the preferred probing nucleobase sequence are also contemplated (eg., less then about 8 subunits, such as about 1, 2, 3, 4, or about 5 subunits), provided hybridization to the intended *Pseudomonas* target sequence is not substantially impaired when compared to the preferred probing nucleobase sequence itself. By the phrase "not substantially impaired" is meant that the modified nucleobase sequence provides sufficient discrimination between target and non-target sequences under suitable hybridization conditions. By the phrase "sufficient discrimination" is meant that a target binding complex and a non-target binding complex exhibit a ΔTm greater than about 2° C., preferably greater than 5° C., most preferably greater than 10° C. eg, between from about 2° C. to about 75° C. Methods of determining such ΔTm are known. By the phrase "suitable hybridization conditions" is meant conditions such as those described by See H. Stender et al., supra. A suitable hybridization condition for performing the analysis includes, but is not limited to, the conditions described below in the Example.

Preferred deletions occur at an end of the sequence, at both ends or between such ends. An example of a substitution in accordance with the invention is T=>U.

Although usually not necessary, the preferred probing nucleobase sequence can be adapted to include at least one of: 1) a subunit deleted therefrom, 2) a subunit added thereto and 3) a substituted subunit; for example, 1, 2, 3, 4, or about 5 of such sequence changes. Such changes can occur at the end of the sequence, at both ends or between such ends as needed. Preferably, hybridization to the intended *Pseudomonas* target is not substantially impaired when compared with preferred probing nucleobase sequence. Hybridization can be determined as discussed above.

A variety of standard procedures exist for monitoring and (if desired) quantifying hybridization between two sequences including, but not limited to, the above-mentioned procedures.

Collectively, the foregoing changes to the sequence of the preferred probing nucleobase sequence are sometimes called "variations" or "variants" to indicate change in sequence with respect to the preferred probing nucleobase sequence (or its complement). Variations of the probing nucleobase sequence are thus considered to be an embodiment of this invention. Common variations have already been described and generally include, deletions, insertions, substitutions and frame shifts. Additionally, a shorter probing nucleobase sequence can be generated by truncation of the sequence identified above. Preferred variations do not substantially impair hybridization when compared to the preferred nucleobase sequence.

Further probes of the invention will comprise at least a probing nucleobase sequence (as previously described herein) and at least one detectable moiety as defined here. Non-limiting examples of additional moieties include linkers, spacers, natural or non-natural amino acids, or other subunits of PNA, LNA, DNA or RNA. Still further variations of the preferred probing nucleobase sequence include certain nucleobase derivatives such as methylcytosine, 2-aminopurine, 2-amino-6-chloropurine, 2,6-diaminopurine, hypoxanthine, pseudoisocytosine, 2-thiouracil, 2-thiothymidine uracil and the like.

Additional probes according to the invention can be labeled with one or a combination of suitable detectable moieties such as one, two or three of same. Internal labeling of the probe is also contemplated. A variety of acceptable moieties have been disclosed herein.

Further probes in accord with the invention are self-indicating (or self-reporting) which probes preferably have a PNA Linear Beacon format as described herein.

Additionally suitable PNA probes of the invention are unlabeled and in some instances may be bound covalently or non-covalently to a suitable solid support. Examples of suitable supports have been disclosed in U.S. Pat. No. 6,664,045, for instance.

Further probes according to the invention will include at least one spacer or linker group that is preferably adapted to help space the detectable moiety from the probing sequence. A variety of suitable spacer/linkers have already been described.

A preferred use of one or combination of the foregoing PNA probes is in the in situ hybridization analysis of *Pseudomonas* (sensu stricto) that is optionally present in a sample. By "optionally present" is meant that the bacteria is known to be in the sample or it is suspected to be in the sample.

As discussed, the invention features a method for the detection, identification and/or quantitation of *Pseudomonas* (sensu stricto) in a sample. The analysis can be accomplished by nearly any procedure including in situ analysis, fluorescence in situ hybridization and the like. Preferred analytical methods do not rely substantially on use of cross-linking reagents or enzymes prior to hybridization between the probing sequence and the intended target. More preferably, the analysis avoids such use entirely and does not involve the use of cross-linking reagents or enzymes prior to hybridization. Particular probing sequences for use with the method include any of the forgoing probes including the preferred nucleobase sequence and variants thereof.

More preferred invention methods involve use to detect a nucleic acid that includes a target sequence in which the nucleic acid has been previously manipulated such as by synthesis or amplification using standard procedures. Preferred nucleic acid synthesis and amplification reactions have already been discussed and include at least one of Polymerase Chain Reaction (PCR), Ligase Chain Reaction (LCR), Strand Displacement Amplification (SDA), Transcription-Mediated Amplification (TMA), Rolling Circle Amplification (RCA) and Q beta replicase, for example.

Practice of the invention is flexible as it can accommodate one or a combination of procedures to improve or otherwise enhance specific binding between an invention probe and the intended target. For instance, and in one embodiment, the method further includes adding at least one blocking probe to method, preferably to reduce or eliminate any hybridization of the PNA probe to non-target sequence.

Use of the invention is also flexible in the sense that it can be used in a wide variety of assay formats. For instance, and in one embodiment, the target sequence is immobilized to a surface. Examples of such surfaces have already been described but generally include suitable polymer or paper supports, beads, and the like. Alternatively, or in addition, a probe of the invention is one component of an array.

Preferred samples for use with the invention are biological samples such as those obtained from blood (including plasma), urine, a secretion, sweat, pus, sputum, stool, mucous or cultures thereof.

As mentioned, the invention also features a kit that has been adapted to perform an assay for detection, identification and/or quantitation of *Pseudomonas* (sensu stricto) in a sample. Typically, such a kit includes a) at least one of the probe disclosed herein such as the preferred nucleobase sequence and b) other reagents or compositions necessary or helpful to perform the assay (eg., sterile water, buffer, and directions for using the kit and the like). By "adapted" is meant that the kit includes a kit component useful for detecting, identifying and/or quantifying *Pseudomonas* in the sample. Examples of such materials include the preferred nucleobase sequence as well as variants thereof. Other examples include one or more components to perform an assay such as an in-situ hybridization or real-time PCR assay.

In one kit embodiment, it will often be helpful to include a positive control such as a sample with a known *Pseudomonas* species. In this invention example, any microorganisms present in the sample can be independently detected, identified and/or quantitated, preferably by reference to the positive control. It will be appreciated that use of the positive control need not accompany every invention application such as when the properties of particular sample or sample set is well known (eg., clinical samples).

A kit in accord with the invention has a wide variety of important applications. In one embodiment, the kit is adapted to detect, identify and/or quantitate the amount of any *Pseudomonas* in a sample in which the sample has been exposed to appropriate antimicrobial agents. The invention is thus particularly useful to monitor the effectiveness of new and known antimicrobials.

Such a kit can be used with one or a combination of detection formats as described herein including, but not limited to, in-situ hybridization assay and a real-time PCR assay. Such kits find particular use in the examination of clinical, industrial, medical, research and foodstuff samples including clinical specimens. The kit may be used with cultures made from the samples if needed. Other kit uses include use in the testing of food, beverages, water, pharmaceutical products, personal care products, dairy products or environmental samples or cultures thereof.

There follows a discussion of more preferred invention embodiments.

II. Preferred Embodiments of the Invention a. PNA Probes

In one embodiment, this invention is directed to PNA probes. The PNA probes of this invention are suitable for detecting, identifying and/or quantitating *Pseudomonas* (sensu stricto) optionally present in a sample. General characteristics (e.g. length, labels, nucleobase sequences, linkers etc.) of PNA probes suitable for the detection, identification and/or quantitation of *Pseudomonas* (sensu stricto) have been previously described herein. The preferred probing nucleobase sequence of PNA probes of this invention are listed in Table 1.

| Sequence ID | Nucleobase sequence |
|---|---|
| Seq. Id. No. 1 | CCT ACC ACC TTA AAC |

The PNA probes of this invention may comprise only a probing nucleobase sequence (as previously described herein) or may comprise additional moieties. Non-limiting examples of additional moieties include detectable moieties (labels), linkers, spacers, natural or non-natural amino acids, or other subunits of PNA, DNA or RNA. Additional moieties may be functional or non-functional in an assay. Generally however, additional moieties will be selected to be functional within the design of the assay in which the PNA probe is to be used. The preferred PNA probes of this invention are labeled with one or more detectable moieties selected from the group consisting of fluorophores, enzymes and haptens.

In preferred embodiments, the probes of this invention are used in in-situ hybridization (ISH) and fluorescence in-situ hybridization (FISH) assays. Excess probe used in an ISH or FISH assay typically must be removed so that the detectable moiety of the specifically bound probe can be detected above the background signal that results from still present but unhybridized probe. Generally, the excess probe is washed away after the sample has been incubated with probe for a period of time. However, the use of self-reporting PNA probes is a preferred embodiment of this invention, since there is no requirement that excess self-indicating probe be completely removed (washed away) from the sample since it generates little or no detectable background. In addition to ISH or FISH assays, self-indicating probes comprising the selected probing nucleobase sequence described herein are particularly useful in all kinds of homogeneous assays such as in real-time PCR or useful with self-indicating devices (e.g. lateral flow assay) or self-indicating arrays.

b. Methods

In another embodiment, this invention is directed to a method suitable for detecting, identifying and/or quantitating *Pseudomonas* (sensu stricto) optionally in a sample. The general and specific characteristics of PNA probes suitable for the detection, identification or quantitation of *Pseudomonas* (sensu stricto) have been previously described herein. Preferred probing nucleobase sequences are listed in Table 1.

The method for detecting, identifying and/or quantitating *Pseudomonas* (sensu stricto) in a sample comprises contacting the sample with one or more PNA probes suitable for hybridization to a target sequence which is unique to all species of the genus *Pseudomonas*. In preferred embodiments, the probe comprises a probing nucleobase sequence wherein at least a portion of the probing nucleobase sequence is complementary to a target sequence of 23S rRNA or rDNA of all species of the genus *Pseudomonas* and with at least one nucleobase difference to the corresponding 23S rRNA or rDNA nucleobase sequences of other bacterium species.

According to the method, *Pseudomonas* (sensu stricto) in the sample is then detected, identified and/or quantitated. Detection, identification and/or quantitation of *Pseudomonas* (sensu stricto) is made possible by correlating hybridization, under suitable hybridization conditions or suitable in-situ hybridization conditions, of the probing nucleobase sequence of a PNA probe to the target sequence of all species of the genus *Pseudomonas* sought to be detected with the presence, absence or number of the *Pseudomonas* (sensu stricto) organisms in the sample. Typically, this correlation is made possible by direct or indirect detection of the probe/target sequence hybrid.

Fluorescence In Situ Hybridization and Real-Time PCR:

The PNA probes, methods, kits and compositions of this invention are particularly useful for the rapid probe-based detection, identification and/or quantitation of *Pseudomonas* (sensu stricto). In preferred embodiments, in-situ hybridization or PCR is used as the assay format for detecting, identifying or quantitating *Pseudomonas* (sensu stricto). Most preferably, fluorescence in-situ hybridization (PNA FISH) or real-time PCR is the assay format. (Reviewed by Stender et al. *J. Microbiol. Methods* 48:1-17 (2002)).

Preferably, smears for PNA FISH analysis are not treated with cross-linking agents or enzymes prior to hybridization.

Exemplary Assay Formats:

Exemplary methods for performing PNA FISH can be found in: Oliveira et., *J. Clin. Microbiol.* 40:247-251 (2002), Rigby et al., *J. Clin. Microbiol.* 40:2182-2186 (2002), Stender et al., *J. Clin. Microbiol.* 37:2760-2765 (1999), Perry-O'Keefe et al., *J. Microbiol. Methods* 47:281-292 (2001). According to one method, a smear of the sample, such as, but not limited to, a positive blood culture, is prepared on microscope slides and covered with one drop of the fluorescein-labeled PNA probe in hybridization buffer. A coverslip is placed on the smear to ensure an even coverage, and the slide is subsequently placed on a slide warmer or incubator at 55° C. for 90 minutes. Following hybridization, the coverslip is removed by submerging the slide into a pre-warmed stringent wash solution and the slide is washed for 30 minutes. The smear is finally mounted with one drop of mounting fluid, covered with a coverslip and examined by fluorescence microscopy.

*Pseudomonas* optimally present in a sample which may be analyzed with the PNA probes contained in the kits of this invention can be detected, identified and/or quantitated by several instruments, such as but not limited to the following examples: microscope (for example see Oliveira et al., *J. Clin. Microbiol* 40:247-251 (2002)), film (for example see Perry-O'Keefe et al., *J. Appl. Microbiol.* 90:180-189) (2001), camera and instant film (for example see Stender et al., *J. Microbiol. Methods* 42:245-253 (2000)), luminometer (for example see Stender et al., *J. Microbiol. Methods* 46:69-75 (2001), laser scanning device (for example see Stender et al., *J. Microbiol. Methods* 45: 31-39 (2001) or flow cytometer (for example see Wordon et al., *Appl. Environ. Microbiol.* 66:284-289 (2000)). Automated slide scanners and flow cytometers are particularly useful for rapidly quantitating the number of microorganisms present in a sample of interest.

Exemplary methods for performing real-time PCR using self-reporting PNA probes can be found in: Fiandaca et al., Abstract, Nucleic Acid-Based technologies. DNA/RNA/PNA Diagnostics, Washington, D.C., May 14-16, 2001, and Perry-O'Keefe et al., Abstract, International Conference on Emerging Infectious Diseases, Atlanta, 2002.

d. Kits

In yet another embodiment, this invention is directed to kits suitable for performing an assay, which detects, identifies and/or quantitates *Pseudomonas* (sensu stricto) optionally present in a sample. The general and preferred characteristics of PNA probes suitable for the detection, identification or quantitation of *Pseudomonas* (sensu stricti) have been previously described herein. Preferred probing nucleobase sequences are listed in Table 1. Furthermore, methods suitable for using the PNA probes to detect, identify or quantitate *Pseudomonas* (sensu stricto) in a sample have been previously described herein.

The kits of this invention comprise one or more PNA probes and other reagents or compositions, which are selected to perform an assay or otherwise simplify the performance of an assay used to detect, identify and/or quantitate *Pseudomonas* (sensu stricto) in a sample.

e. Exemplary Applications for Using the Invention

The PNA probes, methods and kits of this invention are particularly useful for the detection, identification and/or quantitation of *Pseudomonas* (sensu stricto) in clinical samples, food, beverages, water, pharmaceutical products, personal care products, dairy products or environmental samples and cultures thereof.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLE

This invention is now illustrated by the following example, which is not intended to be limiting in any way.

Reference Strains.

The study included reference strains from American Type Culture Collection (ATCC), Manassas, Va. representing *Pseudomonas* species and other non-*Pseudomonas* species, which primarily comprised *Pseudomonas*-like species, including species that were previously included in the *Pseudomonas* genus. An overnight culture grown at 35-37° C. was prepared from each species by standard methods.

Preparation of Smears.

For each smear, one drop of PBS with 1% (v/v) Triton X-100 (Aldrich) was placed in a 8-mm diameter well of a teflon-coated microscope slide (Erie Scientific, Portsmouth, N.H.) and mixed gently with a small drop of re-suspended culture. The slide was then placed on a 60° C. slide warmer for 20 min at which point the smears were dry. Subsequently, the smears were disinfected by immersion into 96% (v/v) ethanol for 5-10 minutes and air-dried.

Fluorescence In Situ Hybridization (FISH).

Smears were covered with approximately 50 µL of hybridization solution containing 10% (w/v) dextran sulfate (Sigma Chemical Co., St. Louis, Mo.), 10 mM NaCl (J. T. Baker), 30% (v/v) formamide (Sigma), 0.1% (w/v) sodium pyrophosphate (Sigma), 0.2% (w/v) polyvinylpyrrolidone (Sigma), 0.2% (w/v) ficoll (Sigma), 5 mM $Na_2EDTA$ (Sigma), 1% (v/v) Triton X-100 (Aldrich), 50 mM Tris/HCl pH 7.5 and 500 nM fluorescein-labeled PNA probe (Flu-OO-CCTACCAC-CTTAAAC) targeting *Pseudomonas* (sensu stricto). Coverslips were placed on the smears to ensure even coverage with hybridization solution, and the slides were subsequently placed on a slide warmer with a humidity chamber (Slidemoat, Boeckel, Germany) and incubated for 90 min at 50° C. Following hybridization, the coverslips were removed by submerging the slides into approximately 20 mL/slide prewarmed 5 mM Tris, pH 10, 15 mM NaCl (J. T. Baker), 0.1% Triton X-100 (Aldrich) in a water bath at 50° C. and washed for 30 min. Each smear was finally mounted using one drop of Mounting Fluid and covered with a coverslip. Microscopic examination was conducted using a fluorescence microscope equipped with a FITC/Texas Red dual band filter set. *Pseudomonas* (sensu stricto) was identified as green fluorescent rods.

The results are listed in the Table 1 below.

| Species | ATCC# | Results |
|---|---|---|
| *Acinetobacter calcoaceticus* | 14987 | Negative |
| *Aeromonas hydrophila* | 7965 | Negative |
| *Brevundimonas diminuta* | 19146 | Negative |
| *Burkholderia cepacia* | 25416 | Negative |
| *Comamonas testosteroni* | 17409 | Negative |
| *Delftia acidovorans* | 15668 | Negative |
| *Pseudomonas aeruginosa* | 9027 | Positive |
| *Pseudomonas aeruginosa* | 27853 | Positive |
| *Pseudomonas alcaligenes* | 14909 | Positive |
| *Pseudomonas chlororaphis* | 9446 | Positive |
| *Pseudomonas fluorescens* | 17397 | Positive |
| *Pseudomonas fluorescens* | 13525 | Positive |
| *Pseudomonas fragi* | 4973 | Positive |
| *Pseudomonas huttiensis* | 14670 | Positive |
| *Pseudomonas luteola* | 35563 | Positive |
| *Pseudomonas mendocina* | 25411 | Positive |
| *Pseudomonas mucidolens* | 4685 | Positive |
| *Pseudomonas nitroreducens* | 33634 | Positive |
| *Pseudomonas pertucinogena* | 190 | Negative |
| *Pseudomonas pseudoalcaligenes* | 12815 | Positive |
| *Pseudomonas putida* | 12633 | Positive |
| *Pseudomonas putida* | 17484 | Positive |
| *Pseudomonas stutzeri* | 11607 | Positive |
| *Pseudomonas veronii* | 700474 | Positive |
| *Ralstonia pickettii* | 27511 | Negative |
| *Sphingomonas paucimobilis* | 29837 | Negative |
| *Stenotrophomonas maltophilia* | 13637 | Negative |

The results show that PNA probe provides accurate identification of *Pseudomonas* species only, whereas other species including *Pseudomonas*-like species were all negative.

According to Table 1, *Pseudomonas pertucinogena* was not detected by the PNA probe. This species belongs to the *Pseudomonas pertucinogena* group, where the other group member *Pseudomonas denitrificans* has been excluded from the *Pseudomonas* genus (Rejection of the species name *Pseudomonas denitrificans* (Christensen) Bergey et al. 1923." Int. J. Syst. Bacteriol. (1982) 32:466). Other studies have shown that *Pseudomonas pertucinogena* is closely related with *Bordetella* species and may therefore not belong in the *Pseudomonas* genus. Even if it is, it is also believed that presence of *Pseudomonas pertucinogena* in a sample used to practice the invention would be rare at best. Thus, the "false negative" shown in Table 1 above is not believed to have any significance and should not be construed to limit the invention in any way.

The invention has been described in detail with reference to preferred embodiments thereof. However, it will be appreciated that those skilled in the art, upon consideration of this disclosure, may make modifications and improvements within the spirit and scope of the invention.

EQUIVALENTS

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein. Such equivalents are intended to be encompassed in the scope of the claims.

The disclosures of all references mentioned herein are incorporated by reference.

What is claimed is:

1. A PNA probe for the detection and/or quantitation of *Pseudomonas* (sensu stricto), wherein the probe consists of CCT ACC ACC TTA AAC (SEQ ID NO: 1).

2. A method for the detection and/or quantitation of *Pseudomonas* (sensu stricto) in a sample, said method comprising:
   a) contacting the sample with a PNA probe consisting of CCT ACC ACC TTA AAC (SEQ ID NO: 1);
   b) hybridizing the PNA probe to a target sequence of *Pseudomonas* (sensu stricto) in the sample; and
   c) detecting the hybridization of the PNA probe to a target sequence as being indicative of presence and/or amount of *Pseudomonas* (sensu stricto) in the sample.

3. A method according to claim 2, wherein the hybridization of the PNA probe to a target sequence takes place in-situ.

4. A method according to claim 2, wherein the hybridization is by fluorescence in-situ hybridization.

5. A method according to claim 4, wherein the hybridization does not involve the use of cross-linking reagents or enzymes prior to hybridization.

6. The method of claim 2, wherein the method is used to detect a nucleic acid comprising a target sequence, wherein said nucleic acid has been synthesized or amplified in a reaction.

7. The method of claim 6, wherein the nucleic acid synthesis or nucleic acid amplification reactions are selected from the group consisting of: Polymerase Chain Reaction (PCR), Ligase Chain Reaction (LCR), Strand Displacement Amplification (SDA), Transcription-Mediated Amplification (TMA), Rolling Circle Amplification (RCA) and Q beta replicase.

8. The method of claim 2, wherein the method further comprises adding at least one blocking probe to reduce or eliminate any hybridization of the PNA probe to non-target sequence.

9. The method of claim 2, wherein the target sequence is immobilized to a surface.

10. The method of claim 2, wherein said PNA probe is immobilized to a surface.

11. The method of claim 10, wherein said PNA probe is one component of an array.

12. The method of claim 2, wherein the sample is a biological sample.

13. The method of claim 12, wherein the biological sample is blood, urine, secretion, sweat, sputum, stool, mucous, or cultures thereof.

* * * * *

UNITED STATES PATENT AND TRADEMARK OFFICE
CERTIFICATE OF CORRECTION

PATENT NO.         : 8,586,314 B2
APPLICATION NO.    : 12/752480
DATED              : November 19, 2013
INVENTOR(S)        : Henrik Stender It is certified that error appears in the above-identified patent and that said Letters Patent is hereby corrected as shown below:

Title Page, Item (56)

On page 1, with respect to the Kempf reference in the right column, *i.e.*, "Kempf et al. Fluorescent in situ hybridization allows rapid identification of microorganisms in blood cultures. *J. Clin. Microbial* 38:830-838 (2000)," replace "*Microbial*" with -- *Microbiol.* --

On page 1, with respect to the second Stender reference in the right column, *i.e.*, "Stender et al. Fluorescence in situ hybridization assay using peptide nucleic acid probes for differentiation between tuberculous and nontuberculous *Mycobacterium* species in smears of *Mycobacterium* cultures. *J. Clin. Microbial.* 37:2760-2765 (1999)," replace "*Microbial.*" with -- *Microbiol.* --

On page 2, with respect to the Woese reference in the left column, *i.e.*, "Woese, Bacterial evolution. *Microbial. Rev.* 51 :221-271 (1987)," replace "*Microbial.*" with -- *Microbiol.* --

Signed and Sealed this
Fourteenth Day of April, 2015

Michelle K. Lee
*Director of the United States Patent and Trademark Office*

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA probe
<220> FEATURE:
<223> OTHER INFORMATION: PNA backbone; see specification as filed for
      detailed description of preferred embodiments

<400> SEQUENCE: 1
cctaccacct taaac                                                   15